United States Patent [19]

Lieberman

[11] 4,282,521

[45] Aug. 4, 1981

[54] REGULATING CIRCUIT FOR GASEOUS IMPURITY DETECTOR

[75] Inventor: Leonard N. Lieberman, La Jolla, Calif.

[73] Assignee: TIF Instruments, Inc., Miami, Fla.

[21] Appl. No.: 93,543

[22] Filed: Nov. 13, 1979

[51] Int. Cl.³ .................... G08B 17/10; G01M 3/04
[52] U.S. Cl. .................... 340/632; 340/634; 73/23; 200/61.03; 330/9; 328/132; 324/130
[58] Field of Search ............... 340/632, 633, 634, 605, 340/659-664, 500, 501; 73/40, 23, 23.1; 200/61.03; 356/437-439, 324; 338/34; 324/224, 225, 130, 71 SN; 328/114,132; 307/232, 350, 152; 330/9

[56] References Cited

U.S. PATENT DOCUMENTS

| | | | |
|---|---|---|---|
| 1,990,706 | 2/1935 | Midgley | 23/230 L |
| 3,439,261 | 4/1969 | Loh et al. | 324/464 |
| 3,460,125 | 8/1969 | Liebermann et al. | 340/632 |
| 3,532,980 | 10/1970 | Tucker | 324/103 R |
| 3,667,041 | 5/1972 | Senour | 324/130 |
| 3,742,475 | 6/1973 | Liebermann et al. | 340/632 |
| 3,786,675 | 1/1974 | Delatorre et al. | 340/632 |
| 3,801,972 | 4/1974 | Ho Kim et al. | 340/634 |
| 3,932,850 | 1/1976 | Conforti et al. | 340/634 |

OTHER PUBLICATIONS

J. Millman, "Micro Electronics, Digital and Analog Circuits and Systems", pp. 596-599, (McGraw-Hill 1979).
J. G. Graeme et al., "Operational Amplifiers, Design and Applications", pp. 350-353(McGraw-Hill 1971).
Stout et al. (Ed.), Handbook of Operational Amplifier Circuit and Design, pp. 25-6 to 25-10 (McGraw-Hill 1976).

Primary Examiner—John W. Caldwell, Sr.
Assistant Examiner—Donnie L. Crosland
Attorney, Agent, or Firm—Pennie & Edmonds

[57] ABSTRACT

A method and apparatus for automatically recalibrating a leak detector. A gaseous impurities is detected by means of a corona discharge. This discharge is sampled and a signal that is a function of the corona discharge level is stored. Subsequent corona discharge levels are compared to the stored signal; and an alarm signal is produced when the subsequent discharge levels exceed the stored value by more than a predetermined amount. To recalibrate the circuit a new signal is stored representative of the corona discharge level at that time. Subsequent corona discharge levels are then compared with the newly stored signal.

16 Claims, 2 Drawing Figures

REGULATING CIRCUIT FOR GASEOUS IMPURITY DETECTOR

TECHNICAL FIELD

This invention relates to a regulating circuit for calibrating an apparatus for the detection of gaseous impurities in an ambient atmosphere.

BACKGROUND ART

Various types of apparatus are known for detecting gaseous impurities, such as halogens, in an ambient atmosphere such as air. Such apparatus rely on various discharge phenomena in the detection of impurities.

In one detection scheme disclosed in U.S. Pat. No. 3,742,475 to Liebermann et al., which is incorporated herein by reference, gaseous impurities are detected by the use of a pulsed corona discharge. A pair of electrodes disposed in an atmosphere under test are repeatedly pulsed with a voltage sufficient to cause a corona discharge in the continuous corona region and the average (d.c.) current component of such discharge is measured. The d.c. signal obtained in accordance with the U.S. Pat. No. 3,742,475 to Liebermann et al. is a highly sensitive indicator of the presence and concentration of gaseous impurities including substances which behave like gaseous impurities, such as air-borne liquids and particulate matter, all of which will be referred to herein by the phrase "gaseous impurities". Of special interest, the corona discharge current level diminishes with increasing concentration of halogen gases. As a result, the Liebermann et al. apparatus is capable of detecting halogen gases in low concentrations making it especially useful in detecting leaks from refrigeration systems utilizing freon and similar halogen-containing refrigerants.

Leak detectors in general must be calibrated to take account of initial conditions because it ordinarily is desirable to detect only significant changes in concentrations with respect to low background concentrations in the ambient atmosphere. Since background levels change with time, weather factors, location etc., and since the sensitivity of the apparatus is affected by use as well as environmental conditions, presently available detectors have to be recalibrated frequently. This is especially so when attempting to detect very low concentrations of an impurity. As will be apparent, manual calibration is time consuming, is frequently a bother, and can be a source of error if not performed carefully.

DISCLOSURE OF THE INVENTION

I have invented a regulating circuit for a leak detector which automatically adjusts for ambient conditions thereby obviating the need to manually recalibrate the leak detector. In accordance with my invention a corona discharge is sampled and a signal that is a function of the corona discharge level is stored. Subsequent corona discharge levels are compared to the stored signal. If the corona discharge changes more than a predetermined amount in comparison to the stored value, an output signal is produced which may be used to trigger an alarm in the leak detector. The circuit may be recalibrated at any later time by storing a new signal representative of the corona discharge level at that time. Subsequent corona discharge levels are then compared to the newly stored signal.

BRIEF DESCRIPTION OF THE DRAWINGS

These and other objects, features and elements of my invention will be more readily apparent from the following detailed description of the drawings in which.

BEST MODE FOR CARRYING OUT THE INVENTION

Figure 1:
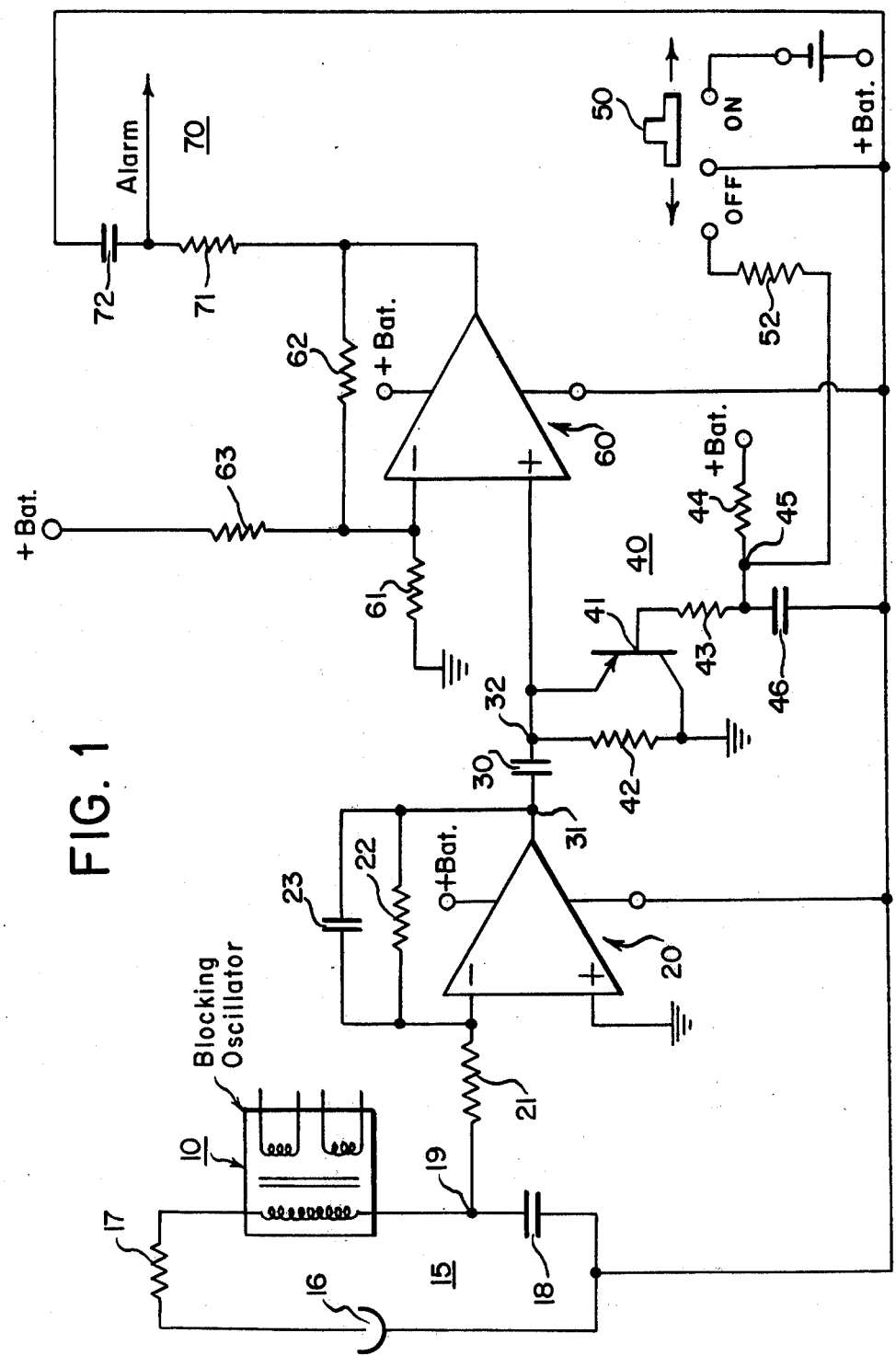
FIG. 1 is a schematic circuit diagram depicting an illustrative embodiment of a leak detector circuit in accordance with the invention.

As shown in FIG. 1, the leak detector circuit comprises a blocking oscillator 10, a corona discharge circuit 15, a first operational amplifier 20, a capacitor 30, a switching circuit 40, a second operational amplifier 60, and alarm circuitry 70. Blocking oscillator 10 and corona discharge circuit 15 are conventional. Circuit 15 comprises an asymmetrical corona electrode pair 16, a resistor 17, the output winding of the blocking oscillator and a capacitor 18. The output winding of the blocking oscillator supplies negative-going pulses to the pointed electrode of corona electrode pair 16 which is disposed in the atmosphere being tested for gaseous impurities. As explained in the above-referenced U.S. Pat. No. 3,742,475, the voltage of these pulses is sufficient to cause a corona discharge across said electrode pair in the continuous corona region; and the average corona discharge current (i.e., the d.c. component of the pulsed current) in this circuit has been found to decrease with increasing concentration of a gaseous impurity such as a halogen. This corona current is averaged (i.e., integrated) by capacitor 18. Illustratively, resistor 17 has a resistance of 100K ohms and capacitor 18 has a capacitance of 0.01 microfarads. Further details of an illustrative blocking oscillator and a corona discharge circuit are set forth in the above-referenced U.S. Pat. No. 3,742,475 to Liebermann et al.

First operational amplifier 20 also includes an input impedance 21 connected to its inverting terminal and a feedback impedance in the form of parallel elements, resistor 22 and capacitor 23. The other end of the input impedance is connected to node 19 between capacitor 18 and the output winding of the blocking oscillator. When the circuit is operating, the voltage at this node is positive with respect to ground. As will be apparent the voltage at node 19 is a measure of the average corona current in circuit 15 and decreases with increasing concentration of a halogen. Illustratively, operational amplifier is one-half of a TL062 available from Texas Instruments, input impedance 21 is a resistor having a resistance of 3.9 megohms, resistor 22 has a resistance of 3.9 megohms and capacitor 23 has a capacitance of 0.05 microfarads. Operational amplifier 20 will be recognized as an inverting amplifier that produces an output signal that is the inverse of the signal at node 19 and it serves to isolate capacitor 30 from the corona discharge circuit.

The output of operational amplifier 20 is connected to a first terminal 31 of a 10 microfarad tantalum capacitor 30. A second terminal 32 of capacitor 30 is connected to switching circuit 40 as well as to the non-inverting input to second operational amplifier 60. As will be described below, capacitor 30 is used to store certain output signals from operational amplifier 20 and to compare other output signals with the signal stored in the capacitor.

Switching circuit 40 comprises a PNP switching transistor 41 whose emitter is connected to the second terminal of capacitor 30, a resistor 42 connecting the emitter and collector of said transistor, resistors 43, 44 and a capacitor 46 connected as shown. Illustratively, switching transistor 41 is a 2N2907 transistor; resistors 42, 43 and 44 have resistances of 10 megohms, 100K ohms and 220K ohms, respectively, and capacitor 46 is a 10 microfarad tantalum capacitor. Switching circuit 40 is controlled by a slide switch 50 which is mounted on the exterior of the leak detector unit (not shown) so that it can easily be operated by the individual testing for leaks. Slide switch 50 includes a resistor 52, one end of which is connected to the node 45 at which resistors 43 and 44 and capacitor 46 are connected. The resistance of resistor 52 is very small (e.g., 100 ohms) compared to that of resistor 44 so that in the OFF position, slide switch 50 and resistor 52 essentially short capacitor 46, discharging any charge that may be stored on capacitor 46. When switch 50 is moved to the ON position, transistor 41 is initially ON, thereby shorting resistor 42 and grounding the second terminal of capacitor 30. However, when switch 50 is in the ON position, capacitor 46 is no longer shorted and the voltage at node 45 gradually becomes positive, eventually turning transistor 41 OFF. The time for node 45 to become positive is determined by the RC time constant of capacitor 46 and resistor 44 and is relatively short (e.g. 2 seconds). With transistor 41 ON, capacitor 30 can be charged or discharged almost instantaneously by the output signal from operational amplifier 20. With transistor 41 OFF, the rate at which capacitor 30 will charge or discharge is determined by the RC time constant of capacitor 30 and resistor 42. Illustratively this time constant is chosen to be relatively long as will be explained below.

Second operational amplifier 60 also includes an input resistor 61, a feedback resistor 62 and a bias resistor 63. Illustratively operational amplifier 60 is the second half of a TL062 available from Texas Instruments, and these resistors have resistances of 20K ohms, 200K ohms and about 26K ohms, respectively. Second operational amplifier will be recognized as a comparator and it serves to produce an output alarm signal when there is a significant change in the average corona current signal as well as to isolate capacitor 30 from the alarm circuitry.

Alarm circuitry 70 comprises a load resistor 71, a filter capacitor 72 and an output lead. Illustratively, load resistor 71 has a 1K ohm resistance and capacitor 72 has a 10 microfarad capacitance. An alarm signal from operational amplifier 60 can be used, for example, to flash a light or sound a buzzer to alert the operator of the presence of a leak.

In operation, switch 50 is initially in the OFF position and capacitor 46 is discharged. As a result when switch 50 is first moved to the ON position, transistor 41 is ON. During the time interval when transistor 41 is ON, the voltage across capacitor 30 very quickly approaches the inverse of the voltage at node 19. Thus, the voltage across capacitor 30 is a measure of the average corona current in circuit 15 at the time switch 50 is initially turned ON. However, when switch 50 is moved to the ON position, capacitor 46 is no longer shorted and the voltage at node 45 eventually becomes positive, thereby turning transistor 41 OFF. Illustratively this occurs one to two seconds after switch 50 is turned ON. When transistor 41 is OFF, the rate at which capacitor 30 will charge or discharge is determined by the RC time constant of capacitor 30 and resistor 42. Illustratively, this time constant is 100 seconds so that any charging or discharging of capacitor 30 while switch 50 is in the ON position takes place over a relatively long period of time.

The charge stored by capacitor 30 represents the average corona current when transistor 41 is ON. If the corona current should vary while switch 50 is in the ON position, a voltage signal will be produced at the output of operational amplifier 20 which is different from the voltage across capacitor 30. Since the voltage across capacitor 30 cannot change instantaneously, the difference between the voltage at the output of operational amplifier 20 and the voltage across capacitor 30 will appear at the noninverting input to amplifier 40. If the rate of change in voltage at the output of operational amplifier 20 is relatively slow (i.e., the change in voltage is relatively small or occurs over a long period of time), the voltage at the input to operational amplifier 60 will not be sufficient to trigger an output signal. If, however, there is a sharp change of voltage at the output of amplifier 20, the signal at the input to amplifier 60 will be sufficiently great to produce an output signal. As will be apparent to those skilled in the art the threshold at which the output signal is produced can be varied by adjusting the resistance of the bias resistor 63.

With a leak detector employing the circuit of FIG. 1, an operator can automatically recalibrate the leak detector in the course of searching for a leak. This eliminates the time lost and the errors that can arise in a manual recalibration. The operator merely slides switch 50 to the OFF position to initiate the recalibration process. This essentially shorts capacitor 46 and turns transistor 41 ON, thereby shorting resistor 42 and grounding second terminal 32 of capacitor 30. A signal representative of mean corona current and therefore the gaseous impurity being sensed by the electrode pair 16 of the leak detector is available at node 19 in the corona circuit. At the output of operational amplifier 20 is a second signal which is a function of the signal at node 19. For the the circuit of FIG. 1, this second signal is the inverse of that at node 19. When switch 50 is moved back from the OFF position to the ON position, this second signal is stored by capacitor 30. In the absence of any gaseous impurity, this signal recalibrates the leak detector at the signal level representative of zero concentration of the impurity. Thereafter, the readings of the leak detector are compared with the signal stored by capacitor 30. In the absence of a leak, these readings will not change appreciably over a short period of time; and the difference between the signal then being read which is available at the output of operational amplifier 20 and the signal stored by capacitor 30 will be slight. Consequently, no alarm signal will be produced. If, however, a leak is detected, the mean corona current will drop significantly. As a result the output signal of amplifier 20 will be considerably different from that stored by capacitor 30; and a difference signal will be produced at the non-inverting input to operational amplifier 60 which is greater than the bias voltage applied to its inverting terminal. Consequently, an alarm signal will be generated alerting the operator of the presence of a leak. Because the calibration of a corona current leak detector is not stable, it is desirable to recalibrate the leak detector frequently during use. This can readily be done simply by sliding switch 50 to the OFF position to initiate the process detailed above.

Figure 2:
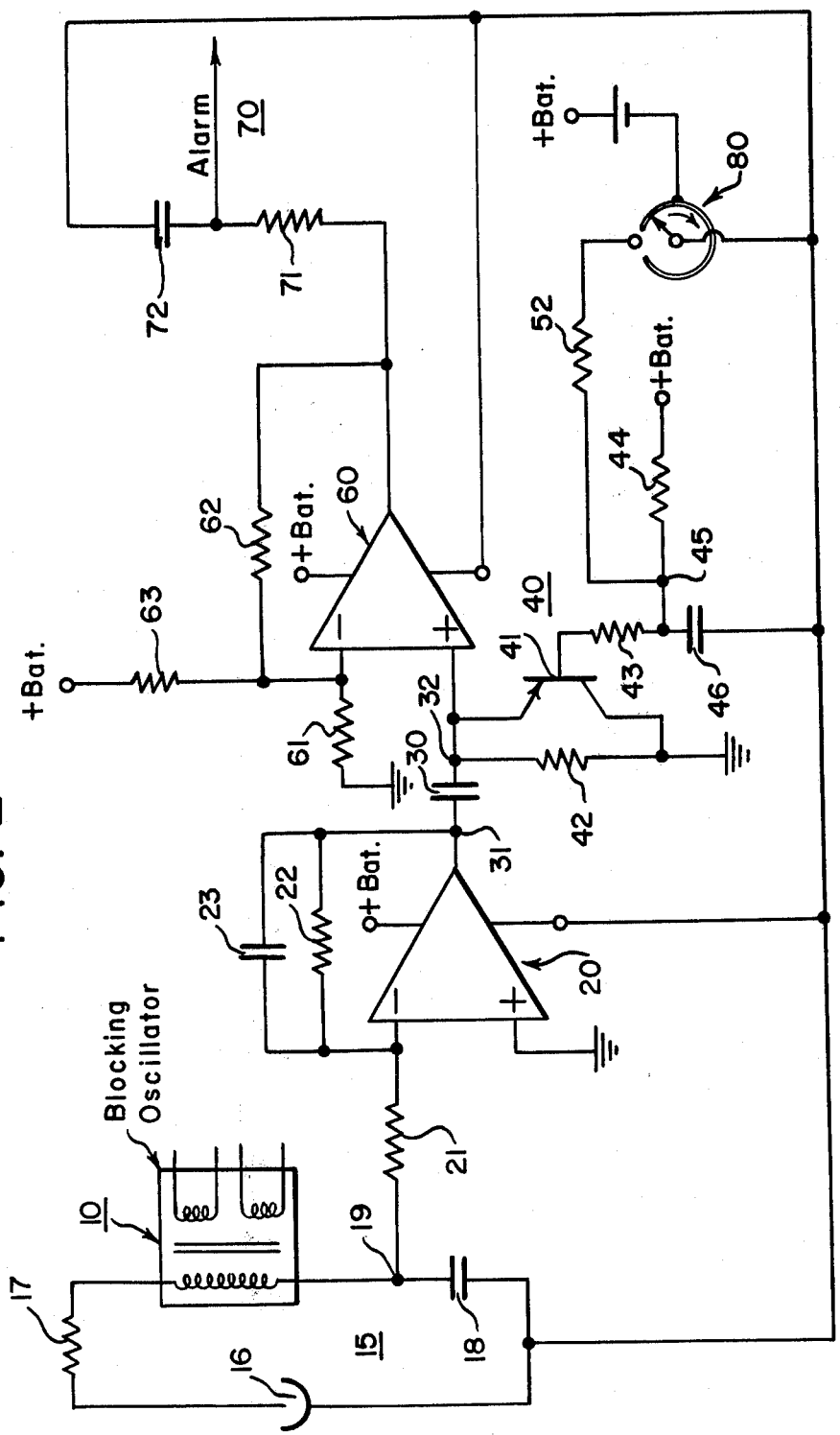
FIG. 2 is a schematic circuit diagram of an alternate embodiment of the invention.

If desired the recalibration process can be initiated automatically by the provision of a timer as shown in FIG. 2. The circuit of FIG. 2 is identical to that of FIG. 1 with the exception that switch 50 has been replaced by a timer 80. Timer 80 operates in a fashion analogous to switch 50 of FIG. 1 and can be embodied in any number of conventional mechanical, electro-mechanical or electronic forms. For most of the duty cycle of timer 80, the timer connects the negative terminal of the power supply, which illustratively is a battery, to one of the terminals of capacitors 18, 46, and 72 as well as to the negative power supply terminals of amplifiers 20 and 60. At regular intervals, timer 80 breaks this connection and connects resistor 52 across capacitor 46 to discharge the capacitor. This operation will be recognized as analogous to the act of moving slide switch 50 of FIG. 1 to the OFF position. Consequently, when timer 80 subsequently disconnects resistor 52 and reconnects the negative terminal of the power supply to the circuit, transistor 41 is turned ON and the second terminal 32 of capacitor 30 is grounded. As a result, the signal available at the output of operational amplifier 20 is stored substantially instantaneously by capacitor 30. After the voltage at node 45 becomes positive, transistor 41 is turned OFF and the circuit of FIG. 2 operates in the same fashion as that of FIG. 1 to compare subsequent readings with that stored by capacitor 30. Periodically timer 80 will again connect resistor 52 across capacitor 46 to begin the process of storing a new value of the mean corona current on capacitor 30. The selection of an appropriate cycle time for timer 80 will depend on the particular application of the leak detector.

While the specific circuit described above has been designed for use with a halogen leak detector, it will be recognized by those skilled in the art that it is generally applicable to circuits which use a corona current to detect the presence of gaseous impurities. Numerous alternatives to the circuits described will be apparent to those skilled in the art from the foregoing description of the invention.

What is claimed is:

1. Apparatus for detecting gaseous impurities in an atmosphere comprising:
   an asymmetrical electrode pair disposable in said atmosphere;
   means for forming a corona discharge across said electrode pair in the continuous corona region;
   means for forming a first signal representative of the mean corona current of said discharge, said signal being representative of the concentration of the gaseous impurity;
   means for forming a second signal which is a function of said first signal;
   means for storing said second signal relatively rapidly, whereby there is recorded a representation of said mean corona current at the time said second signal is stored, and for updating relatively slowly the signal that is stored;
   switching means having at least two operative states, said second signal being stored relatively rapidly when said switching means is in a first state and said stored signal being updated relatively slowly when said switching means is in a second state; and
   means for sensing a change in the mean corona current relative to said stored signal and for producing an output signal when said change in the mean corona current is greater than a predetermined amount.

2. The apparatus of claim 1 wherein said means for forming a second signal, said means for storing and for updating, and said means for sensing and for producing comprise a capacitor, a resistor, and first and second operational amplifiers in which:
   said first signal is applied to an inverting input terminal of the first operational amplifier and said second signal is produced at an output terminal of said amplifier,
   said output signal is derived from an output terminal of the second operational amplifier;
   the capacitor is connected in series between said output terminal of the first operational amplifier and a non-inverting input terminal of the second operational amplifier; and
   said resistor is connected to form an RC-network with said capacitor, said resistor being shunted by a low resistance path when said switching means is in said first state.

3. The apparatus of claim 2 wherein the RC time constant of said resistance and said capacitor is on the order of 100 seconds.

4. Apparatus for detecting gaseous impurities in an atmosphere comprising:
   an asymmetrical electrode pair disposable in such atmosphere;
   means for forming a corona discharge across said electrode pair in the continuous corona region;
   means for forming a first signal representative of the mean corona current of said discharge, said signal being representative of the concentration of the gaseous impurity;
   a first operational amplifier, said first signal being applied to a non-inverting input terminal of said amplifier, said amplifier producing at an output terminal a second signal which is a function of said first signal;
   a second operational amplifier for producing an output signal when said mean corona current changes by more than a predetermined amount;
   a capacitator connected in series between said output terminal of said first operational amplifier and a non-inverting input terminal of said second operational amplifier, said capacitor providing means for storing said second signal, whereby there is recorded a representation of said mean corona current at the time said second signal is stored;
   switching means having at least two operative states, said second signal being stored relatively rapidly when said switching means is in a first state and said stored signal being updated relatively slowly when said switching means is in a second state; and
   a resistor connected to form an RC-network with said capacitor, said resistor being shunted by a low resistance path when said switching means is in said first state.

5. The apparatus of any one of claims 2 or 4 further comprising means for changing said second signal stored by said capacitor to make it a function of a subsequent first signal representative of the mean corona current, whereby said apparatus is recalibrated for changes in the mean corona current.

6. The apparatus of any one of claims 1, 2 or 4 wherein said means for forming a corona discharge is a source of voltage pulses connected to said electrode pair, the voltage of said pulses being sufficient to cause said corona discharge.

7. The apparatus of any one of claims 2 or 4 further comprising means for automatically changing said second signal stored by said capacitor to make it a function of a subsequent first signal representative of the mean corona current, whereby said apparatus is recalibrated for changes in the mean corona current.

8. The apparatus of claim 4 wherein the RC time constant of said resistance and said capacitor is on the order of 100 seconds.

9. The apparatus of claim 2 or claim 4 wherein said resistor is connected in series between ground and a terminal of the capacitor which is connected to the non-inverting input terminal of the second operational amplifier and said switching means selectively grounds said terminal whereby said capacitor may be changed substantially instantaneously with said second signal when said terminal is grounded.

10. The apparatus of claim 2 or claim 4 wherein said switching means comprises a transistor and said apparatus further comprises a manually operated switch, a voltage source, and a capacitor, said manually operated switch has at least two operating states in a first one of which said capacitor is essentially shorted and in the second of which said capacitor is charged by said voltage source, and said transistor provides a low resistance shunt path across said resistor when said capacitor is essentially shorted and becomes non-conductive a fixed time after said voltage source begins to charge said capacitor, whereby, when said manually operated switch is changed from said first state to said second state, said second signal is stored in the capacitor connected between said operational amplifiers within said fixed time and said low resistance shunt path across said resistor is then removed.

11. A method of detecting gaseous impurities in an atmosphere comprising the steps of:

forming a corona discharge across a pair of electrodes in the continuous corona region, said electrodes being disposed in said atmosphere;

forming a first signal representative of the mean corona current of said discharge, said signal being representative of the concentration of the gaseous impurity;

forming a second signal which is a function of said first signal;

at selected times, storing said second signal relatively rapidly, whereby there is recorded a representation of said mean corona current at the time said second signal is stored, and at other times updating relatively slowly the signal that is stored;

sensing a change in the mean corona current relative to said stored second signal; and producing an output signal when said change in the mean corona current is greater than a predetermined amount.

12. The method of claim 11 wherein the step of forming a corona discharge comprises the step of applying voltage pulses across said pair of electrodes, the voltage being sufficient to cause said corona discharge.

13. The method of claim 11 further comprising the step of changing said second signal stored by said capacitor to make it a function of a subsequent first signal representative of the mean corona current, whereby said apparatus is recalibrated for changes in the mean corona current.

14. The method of claim 13 wherein said changing step is performed automatically without operator intervention.

15. The method of claim 11 wherein:

the first signal is applied to an inverting input terminal of a first operational amplifier and the second signal is produced at an output terminal of said amplifier;

the output signal is derived from an output terminal of a second operational amplifier;

the second signal is stored by a capacitor connected in series between the output terminal of the first operational amplifier and a non-inverting input terminal of the second operational amplifier; and a resistor is connected to form an RC-network with said capacitor, said resistor being shunted by a low resistance path to store said second signal relatively rapidly in said capacitor.

16. The method of claim 15 wherein said resistor is connected in series between ground and a terminal of the capacitor which is connected to the non-inverting input terminal of the second operational amplifier, said method further comprising the step of selectively grounding said terminal, whereby when the terminal is grounded said capacitor is charged substantially instantaneously with the second signal.

* * * * *

REEXAMINATION CERTIFICATE (1188th)
United States Patent [19]

Lieberman

[11] B1 4,282,521

[45] Certificate Issued  Jan. 16, 1990

[54] REGULATING CIRCUIT FOR GASEOUS IMPURITY DETECTOR

[75] Inventor: Leonard N. Lieberman, La Jolla, Calif.

[73] Assignee: TIF Instruments, Inc., Miami, Fla.

Reexamination Request:
No. 90/001,733, Mar. 27, 1989

Reexamination Certificate for:
Patent No.: 4,282,521
Issued: Aug. 4, 1981
Appl. No.: 93,543
Filed: Nov. 13, 1979

[51] Int. Cl.⁴ .................. G08B 17/10; G01M 3/04
[52] U.S. Cl. .................................. 340/632; 340/634; 73/23; 200/61.03; 324/130; 328/132; 330/9
[58] Field of Search ............... 340/632, 634, 633, 605, 340/659-664, 500, 501; 73/23, 23.1, 140; 200/61.03; 330/9; 356/437-439, 324; 338/34; 324/224, 225, 130, 71.1; 328/114, 132; 307/232, 350, 152

[56] References Cited
U.S. PATENT DOCUMENTS

| Re. 32,552 | 12/1987 | Liebermann et al. | 340/632 |
| 1,990,706 | 2/1935 | Midgley | 23/230 L |
| 2,550,498 | 4/1951 | Rice | 324/468 |
| 3,076,139 | 1/1963 | Roberts |  |
| 3,438,259 | 4/1969 | Bossert, Jr. |  |
| 3,439,261 | 4/1969 | Loh et al. | 324/464 |
| 3,460,125 | 8/1969 | Liebermann et al. | 340/632 |
| 3,532,980 | 10/1970 | Tucker | 324/103 R |
| 3,667,041 | 5/1972 | Semour | 324/130 |
| 3,728,615 | 4/1973 | Hill et al. | 340/632 |
| 3,742,475 | 6/1973 | Liebermann et al. | 340/632 |
| 3,786,675 | 1/1974 | Delatorre et al. | 340/632 |
| 3,801,972 | 4/1974 | Kim et al. | 340/634 |
| 3,932,850 | 1/1976 | Conforti et al. | 340/634 |
| 4,080,074 | 3/1978 | French | 356/88 |

OTHER PUBLICATIONS

J. Millman, "Micro Electronics, Digital and Analog Circuits and Systems", pp. 596-599, (McGraw-Hill, 1979).
J. G. Graeme et al, "Operational Amplifiers, Design and Applications", pp. 350-353 (McGraw-Hill, 1971).
Stout et al, (Ed), Handbook of Operational Amplifier Circuit and Design, pp. 25-6 to 25-10 (McGraw-Hill 1976).

*Primary Examiner*—Donnie L. Crosland

[57] ABSTRACT

A method and apparatus for automatically recalibrating a leak detector. A gaseous impurities is detected by means of a corona discharge. This discharge is sampled and a signal that is a function of the corona discharge level is stored. Subsequent corona discharge levels are compared to the stored signal; and an alarm signal is produced when the subsequent discharge levels exceed the stored value by more than a predetermined amount. To recalibrate the circuit a new signal is stored representative of the corona discharge level at that time. Subsequent corona discharge levels are then compared with the newly stored signal.

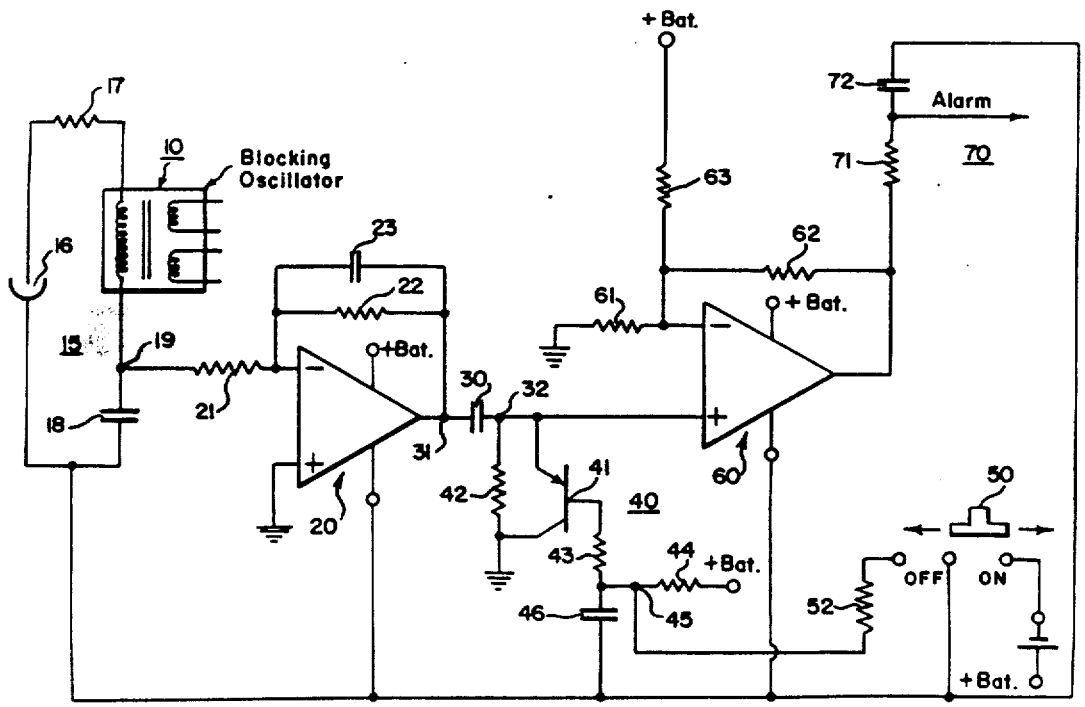

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-16 is confirmed.

* * * * *